United States Patent
Vidal et al.

[11] Patent Number: 6,056,758
[45] Date of Patent: *May 2, 2000

[54] APPARATUS AND METHODS FOR IOL INSERTION

[75] Inventors: Claude A. Vidal, Santa Barbara; Michael Collinson; Alan K. Plyley, both of Goleta, all of Calif.

[73] Assignee: Allergan, Waco, Tex.

[*] Notice: This patent is subject to a terminal disclaimer.

[21] Appl. No.: 08/928,971

[22] Filed: Sep. 12, 1997

Related U.S. Application Data

[63] Continuation of application No. 08/592,163, Jan. 26, 1996, Pat. No. 5,776,138.

[51] Int. Cl.$^7$ .......................................... A61F 9/00
[52] U.S. Cl. .............................. 606/107; 623/6
[58] Field of Search .................. 606/107; 623/4, 623/6; 604/57–64; 222/630–632

[56] References Cited

U.S. PATENT DOCUMENTS

| | | |
|---|---|---|
| 4,681,102 | 7/1987 | Bartell . |
| 4,785,810 | 11/1988 | Buccala et al. . |
| 4,836,201 | 6/1989 | Patton et al. ............... 606/107 |
| 4,919,130 | 4/1990 | Stoy et al. ................. 606/107 |
| 4,934,363 | 6/1990 | Smith et al. . |
| 5,190,552 | 3/1993 | Kelman . |
| 5,474,562 | 12/1995 | Orchowski et al. . |
| 5,494,484 | 2/1996 | Feingold . |
| 5,496,328 | 3/1996 | Nakajima et al. . |
| 5,499,987 | 3/1996 | Feingold . |
| 5,535,746 | 7/1996 | Hoover et al. . |
| 5,551,448 | 9/1996 | Matula et al. . |
| 5,728,102 | 3/1998 | Feingold et al. .......... 606/107 |
| 5,735,858 | 4/1998 | Makker et al. ............ 606/107 |
| 5,776,138 | 7/1998 | Vidal et al. ............... 606/107 |

FOREIGN PATENT DOCUMENTS 49404 4/1993 Japan .

*Primary Examiner*—Glenn K. Dawson
*Attorney, Agent, or Firm*—Stout, Uxa, Buyan & Mullins; Frank J. Uxa

[57] ABSTRACT

Apparatus and method for inserting intraocular lenses (IOLs) into eyes. The apparatus includes a tube, an elongated member having a tip secured to its distal end, and a rod having a distal end portion. The tip is softer than the distal end of the elongated member.

13 Claims, 5 Drawing Sheets

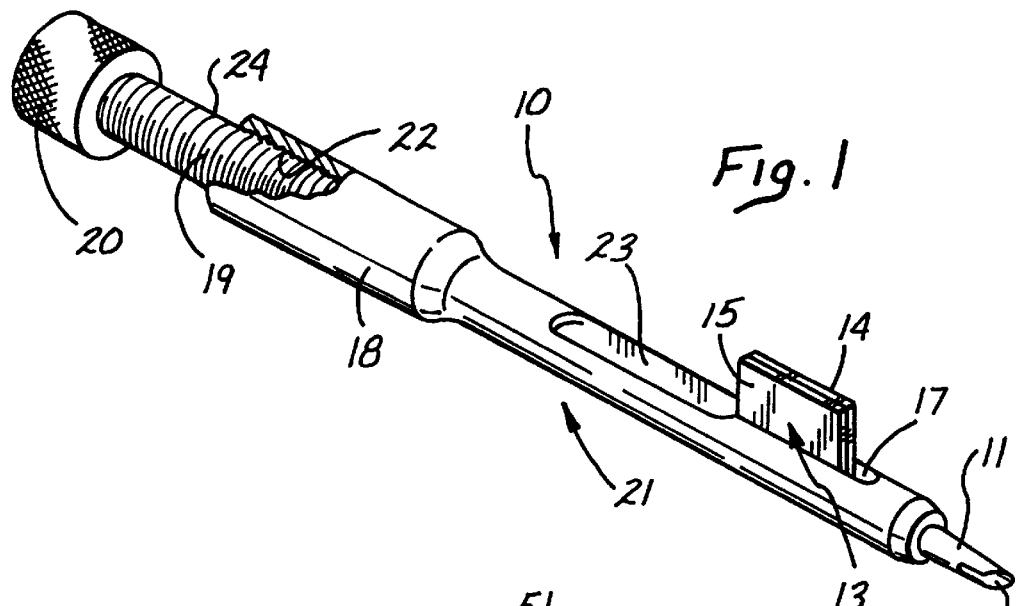
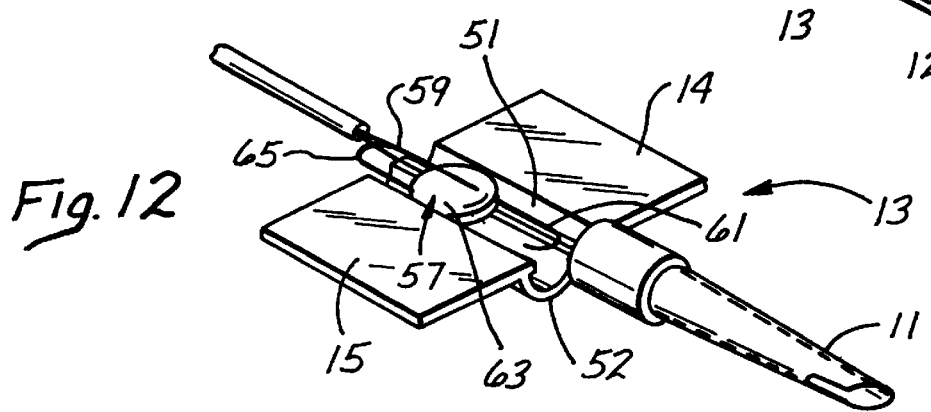
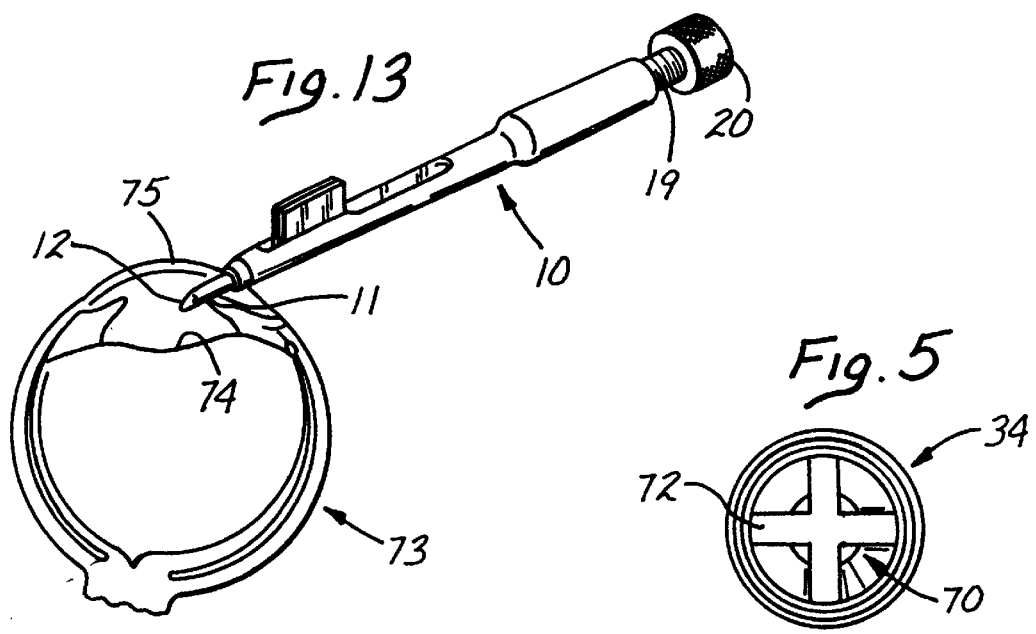
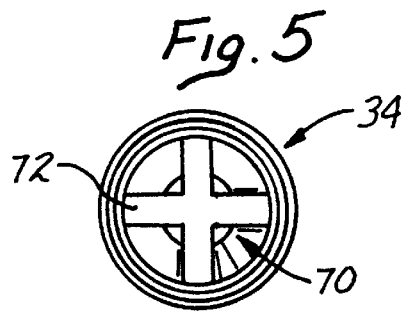

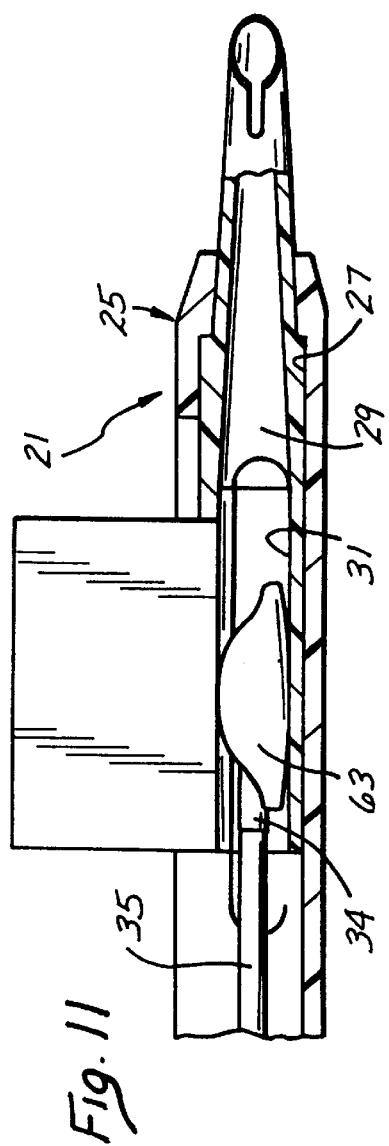
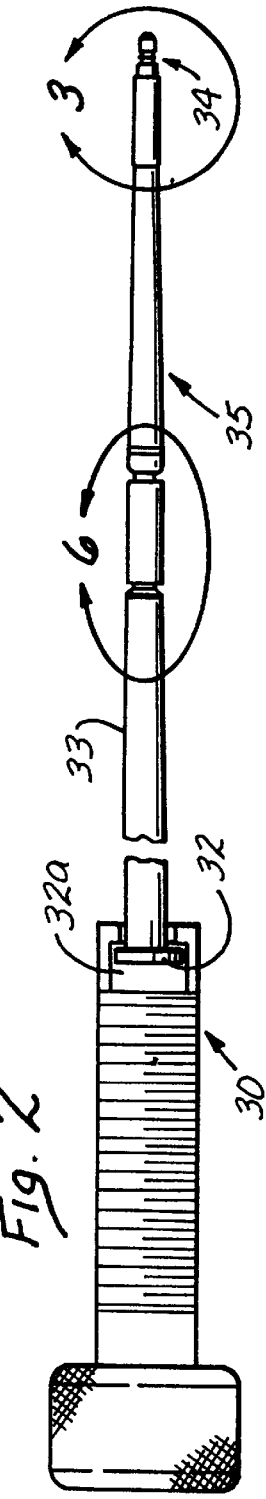
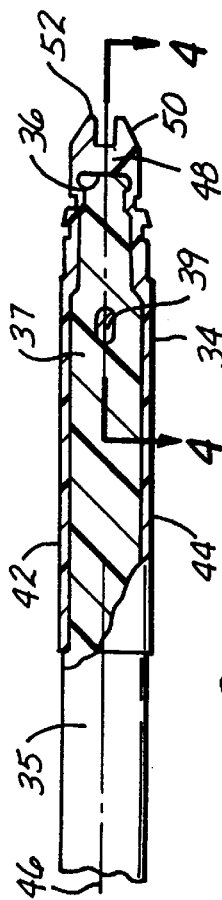
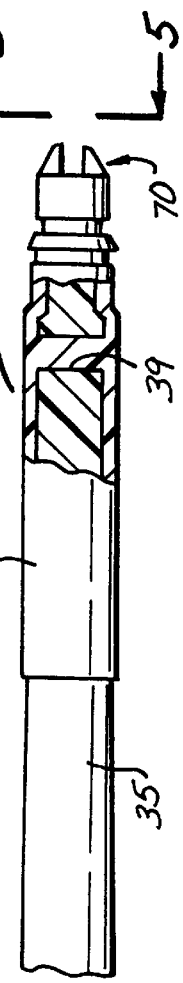

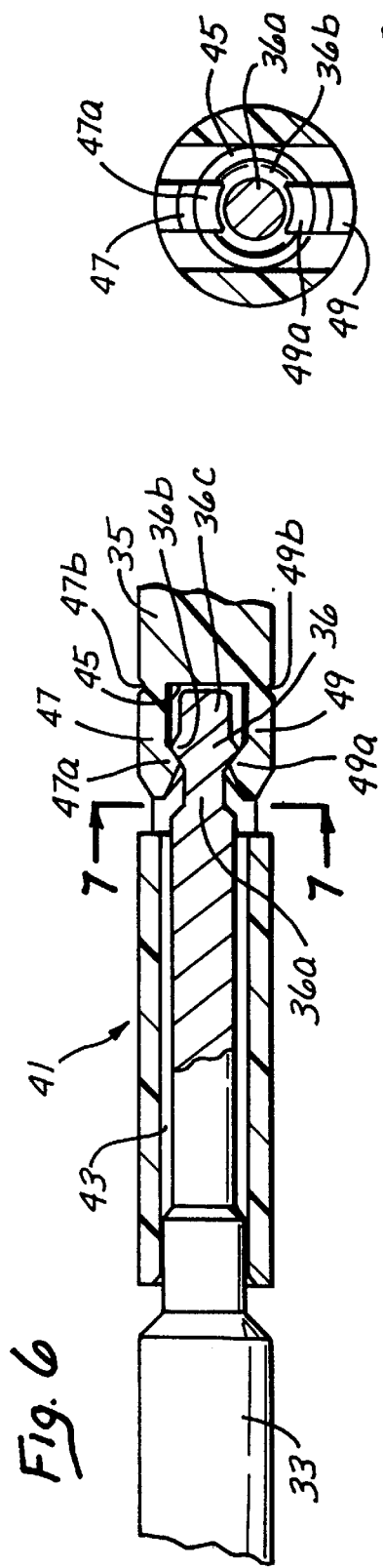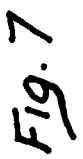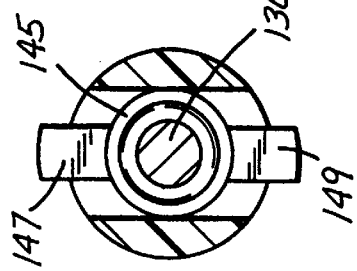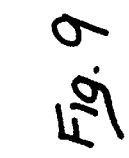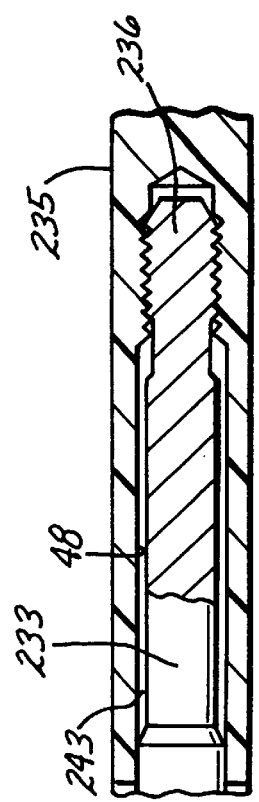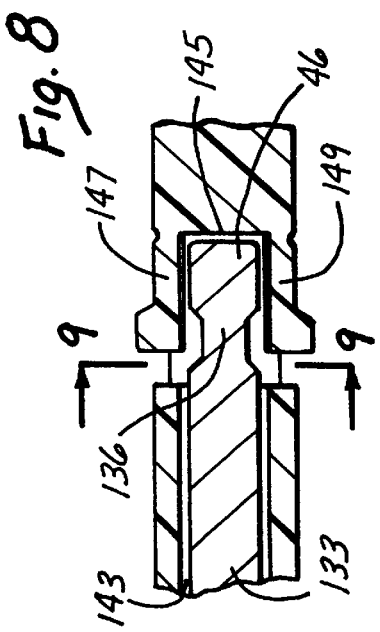

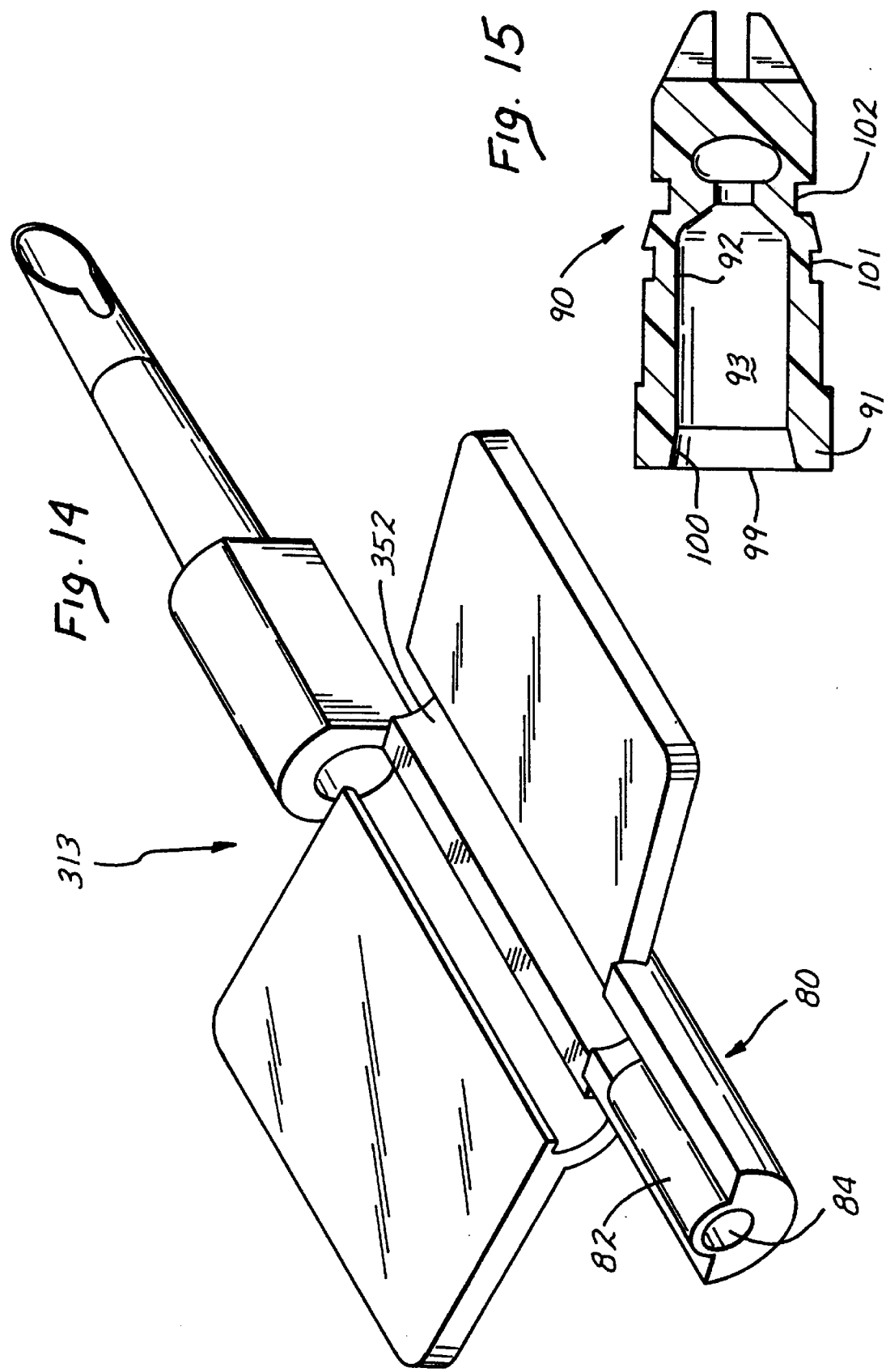

APPARATUS AND METHODS FOR IOL INSERTION

This application is a continuation of 08/592,163, filed Jan. 26, 1996, now U.S. Pat. No. 5,776,138.

BACKGROUND OF THE INVENTION

The present invention relates to apparatus and methods for inserting an intraocular lens into an eye. More particularly, the invention relates to such apparatus and methods wherein the desired insertion of the lens is easily, controllably and effectively achieved.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic, which extends from the optic and becomes affixed in the eye to secure the lens in position. The optic of the IOL normally includes an optically clear lens. Implantation of such IOLs into the eye involves making an incision in the eye. Making the incision as small as possible reduces trauma and speeds healing.

IOLs are known which are foldable (deformable) so that the IOL can be inserted into the eye through an incision smaller than the diameter of the lens and subsequently permitted to unfold after it has passed through the incision. A substantial number of instruments have been devised to aid in inserting such a foldable lens into the eye. The advantages of the foldable lens in cataract removal and lens replacement are so significant that many of the lens replacement procedures are performed with folded lenses inserted into the eye, and released therein to assume their initial unfolded state.

Some of the most generally accepted insertion apparatus employ a hollow insertion tube having a diameter which permits the folded IOL to pass through the hollow space defined by the tube without permanent deformation, and a plunger assembly including a rod, often made of metal, which is moved longitudinally in the hollow space in contact with the optic of the IOL to push the IOL through the hollow space.

Several disadvantages are apparent in such insertion devices. For example, pushing, without trapping or holding, the IOL through and out of the hollow space defined by the tube can cause the IOL to be released from the insertion device without precise control, so that the released IOL may damage the eye and/or may be mispositioned in the eye. In addition, the metal rod can result in marking the surface of the optic and/or even tearing the optic, particularly when the optic is made of soft materials, such as soft elastomeric silicone polymeric materials. Also, the metal rod has a tendency to by-pass the IOL in the hollow space. That is, the rod as it is being moved distally through the hollow space may actually pass through a fold in the folded optic. If this occurs, the rod becomes ineffective to push the IOL through the hollow space. This problem has been avoided in the past by increasing the cross-sectional area of the rod. However, a rod with a large cross-sectional area presents its own problems. For example, pushing such a large rod through the hollow space can damage the IOL and/or the inserter or result in an uncontrolled release of the IOL into the eye, possibly with inserter debris being disadvantageously introduced into the eye.

Stoy et al U.S. Pat. No. 4,919,130 discloses a rod-type IOL insertion device including two separate rods. This patent discloses a cup-shaped head of soft material, such as a silicone elastomer, detachably connected at the distal end of the second rod which pushes a compressed IOL through the cannula or tube. Although this cup-shaped head may avoid scratching or tearing the lens during the pushing operation, its cup-shaped distal face does nothing to increase the control the surgeon has in releasing the IOL in the eye. In addition, this cup-shaped head is relatively short, in the axial direction, which can result in the head becoming separated from the rod in the eye. This can result in an additional procedure to remove the head from the eye, which is traumatic for the patient.

One further disadvantage of using a soft head or tip is the need to place the head or tip on the rod and then to remove it, for example, after use for disposal. Because such heads tend to be relatively small, it is often difficult and time and labor consuming to apply the head to the rod manually and to remove the head from the rod manually.

The disclosure of commonly assigned U.S. patent application Ser. No. (Attorney's Docket No. D-2710) filed on even date herewith is incorporated by reference in its entirety herein.

It would be advantageous to provide IOL insertion apparatus and methods which facilitate the use of soft heads or tips to enhance the advantages of using such soft heads or tips on the rods of IOL insertion apparatus.

SUMMARY OF INVENTION

New apparatus for inserting IOLs and methods for inserting IOLs into eyes have been discovered. The present apparatus and methods solve one or more of the problems of the prior art systems, such as those problems noted above. The present apparatus enable the surgeon to effectively and efficiently achieve a desired degree of control as the IOL is released from the apparatus, while, at the same time, making it easier and less time and labor consuming to do so. The present invention is straightforward, easy to make and practice and involves little or no modification of existing surgical techniques. Also, the IOLs do not need to be modified to accommodate the present apparatus and methods.

In one broad aspect, the present invention comprises apparatus for inserting IOLs into an eye which include a tube defining a hollow passage, for example, through at least a portion of which a folded IOL can be moved. This tube has a port, preferably at its distal end, through which the IOL is passed from the hollow passage into an eye. An elongated member is provided which is longitudinally movable within the hollow space and has a distal end portion and a proximal end portion. A rod is also included, is longitudinally movable and has a distal end region which is coupled, preferably removably coupled, to the elongated member, for example, at the proximal end region of the elongated member. A tip is secured, preferably permanently secured, to the elongated member and extends distally from the distal end portion of the elongated member. This tip is softer, and preferably more elastic, than the distal end portion and is sized and configured so that at least a portion of the tip comes in contact with the folded IOL as the elongated member is moved distally in the hollow space. The rod and the elongated member may be made of metal, a relatively rigid or non-elastic polymeric material or combinations thereof. The elongated member preferably is made of polymeric material.

Preferably, the elongated member is made of a first polymeric material and the tip is made of a different, second polymeric material. The elongated member is preferably at least somewhat rigid, for example, more rigid then the tip, to allow effective transfer of forces from the rod to the tip.

Any suitable method may be employed to produce the tip/elongated member combination. One very useful production method is insert molding. For example, the elongated member can be formed and then included in a mold in which the tip is formed onto the distal end portion of the elongated member, for example, using conventional insert molding techniques. The elongated member preferably includes at least one through hole and a portion of the tip is located in this through hole, thereby facilitating the permanent securement of the tip to the elongated member.

In one embodiment, the elongated member defines a cavity, preferably includes a plurality of elements defining a cavity, in which the distal end region of the rod is maintained. More preferably, the plurality of elements and the distal end region of the rod are configured to facilitate the distal end region passing into the cavity as the rod is moved longitudinally toward the elongated member and to resist the distal end region passing out of the cavity as the rod is moved longitudinally away from the elongated member. For example, the plurality of elements may be adapted to flex as the distal end region is passed distally into the cavity. The distal end region of the rod may be interference-fitted or friction-fitted into the cavity. Still further, the distal end region of the rod may be threaded and the elongated member may include threads, for example, on the inner sidewall of the cavity, which matingly engage the distal end region of the rod.

In any event, the rod is coupled to the elongated member.

In another broad aspect of the present invention, apparatus for holding a folded IOL prior to insertion in an eye are provided. Such apparatus comprise a tube and a tip holder. The tube defines a hollow space in which a folded IOL is maintained prior to insertion in an eye. The tube has a port through which the IOL is passed from the hollow space into an eye. The tip holder is positioned proximally of the hollow space and is adapted to hold a tip prior to the tip being carried by a rod which is longitudinally moveable within the hollow space.

In this aspect of the invention, the tip is preferably picked up by the rod as the rod is moved distally toward the hollow space. More preferably, the tip is removed from the rod as the rod moves proximally away from the hollow space.

The tip holder preferably defines a through space substantially aligned with the hollow space and through which the rod passes prior to entering into the hollow space. The tip holder is preferably adapted to resist the tip separating from the tip holder as the rod is moved distally into the through space. More preferably, the tip holder is adapted to facilitate the removal of the tip from the rod as the rod is moved proximally away from the hollow space. For example, the tip holder may include a lip extending into the through space which is adapted to remove the tip from the rod as the rod is moved proximally from the hollow space.

In one very useful embodiment, the tube and tip holder combination further comprises a tip held by the tip holder.

IOL loading cartridges including the tube and the tip holder in accordance with the present invention, can be manufactured, for example, molded as an integral unit. This unit, which is preferably made of substantially rigid polymeric material, can be very effectively used, for example, in conjunction with a rod and hand piece, and then disposed of in a cost effective manner.

The tip in accordance with the present invention may be of any suitable configuration, provided that it functions as described herein. The tip preferably has a configuration such that (1) at least a portion of the tip is trapped or held by the IOL (the IOL may be considered to be trapped by the tip); and/or (2) the tip does not bypass the IOL during the insertion process; and/or (3) the tip does not cause significant or undue damage to the IOL. More preferably, at least two of these criteria are met, and still more preferably all three of the criteria are met.

The tip is preferably made of a polymeric material, particularly an elastomeric polymeric material, such as an elastomeric silicone polymeric material.

In one very useful embodiment, the tip is sized and configured so that at least a portion of the tip is introduced into a fold of the folded IOL as the elongated member and/or the rod is moved distally in the hollow space. More preferably, the tip is sized and configured so that at least a portion of the tip is held or trapped in a fold of the folded IOL as the elongated member and/or the rod is moved distally in the hollow space. These features of the present invention preferably result in the folded IOL being passed through the hollow space of the tube other than by pushing, even through the elongated member and/or the rod and the tip are being moved distally. The folded IOL can be considered as being carried by and/or pulled by the elongated member and/or the rod/tip combination. The advantage of this non-pushing mode of passing the IOL through the hollow space is increased control. That is, the surgeon has an increased degree of control, relative to pushing the IOL through the hollow passage, of the movement of the IOL through the hollow passage of the tube and the release of the IOL into the eye.

If an elongated member is employed, the present tip is secured, preferably permanently secured, to the elongated member. Since the elongated member preferably has sufficient length to allow easy and rapid coupling to the rod, having the tip secured, preferably permanently secured, to the elongated member greatly facilitates including the tip in the present system. Also, since it is preferred that the tip be disposed of after a single use, and, while much of the remainder of the present system is made of metal and can be reused after sterilization, the use of the elongated member/tip combination is very effective for rapid changing of the tip.

The tip preferably has a proximal end segment having an outer surface which defines a cross-sectional area which is larger than the cross-sectional area defined by the outer surface of any other segment of the tip. The proximal end segment of the tip preferably is larger in cross-sectional area than is the distal end segment of the tip. This feature, which may be considered to be a distal tapering of the tip, allows the tip to more effectively and efficiently enter a fold of the IOL and to become held or trapped by the folded IOL. A particularly useful embodiment provides that the distal end segment defines a smaller cross-sectional area than does that defined by the outer surface of the proximal end of the tip. Very effective results are obtained by providing the tip with a proximal end segment which is substantially tapered. For example, at least a portion of the tip which extends distally beyond the elongated member and/or the rod may have a generally conical or truncated conical configuration which facilitates the introduction of the tip into a fold of the folded IOL.

The tip of the present apparatus preferably is itself sufficiently elongated so that when the tip is being held in a fold of the folded IOL the optic of the IOL is not in direct contact with the elongated member and/or the rod. That is, for example, the tip has sufficient length so that the optic of the folded IOL comes in direct contact only with the tip as the elongated member and/or the rod is moved distally in the hollow space defined by the tube. This feature provides substantial benefits, for example, in that the optic is prevented from contacting the elongated member and/or the rod, which may cause scratching or tearing of the optic. Excellent results are obtained with a tip having a length in the range of about 1 mm to about 5 mm or 10 mm or about 50 mm, although other lengths may be suitable. In one embodiment, the proximal end segment of the tip is longer than all the other segments of the tip combined.

In another broad aspect of the present invention, methods for inserting an IOL into an eye are provided. These methods comprise placing an IOL in a folded condition in the tube/tip holder/tip-containing apparatus described herein; moving a rod distally relative to the tip holder to position the tip on the rod; moving the rod further distally into the hollow space defined by the tube, thereby contacting the tip and the IOL; positioning the port of the tube in proximity to or in the eye; passing the IOL through the hollow space, through the port and into the eye; passing the rod proximally; and removing the tip from the rod. The positioning of the tip on the rod and the removing of the tip from the rod preferably occur substantially automatically, for example, simply by moving the rod distally into the hollow space and then moving the rod proximally out of the hollow space.

An important advantage of the present methods is that the IOL can be passed into the eye through an incision in the eye no larger than about 3.5 mm, more preferably no larger than about 3.0 mm. Also, because the tip preferably is "automatically" positioned on the rod and removed from the rod, as desired, the tedious task of manually applying and removing the tip from the rod is eliminated. This facilitates the use of the tip, and more conveniently allows the attainment of the benefits of the tip. Also, since the tip is removed after use, much of the remainder of the apparatus, for example, the rod and the hand piece, can be sterilized and reused repeatedly.

Each of the individual features of the present invention disclosed herein may be used alone or in combination with one or more other of such features, provided such features are not mutually consistent with each other. All apparatus and methods involving any such feature or combination of such features are included within the scope of the present invention.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 1 is a side perspective view of an insertion apparatus in accordance with the present invention.

FIG. 2 is a side view, partly in cross-section, of the rod-plunger assembly removed from the body of the insertion apparatus shown in FIG. 1.

FIG. 3 is a side view, partly in cross-section, of the area within the arc 3 of FIG. 2.

FIG. 4 is a view, partly in cross-section, taken generally along line 4—4 of FIG. 3.

FIG. 5 is a view taken generally along line 5—5 of FIG. 4.

FIG. 6 is a side view, partly in cross-section, of the area within the arc 6 of FIG. 2 showing the coupling of the rod and elongated member.

FIG. 7 is a cross-sectional view taken generally along lines 7—7 of FIG. 6.

FIG. 8 is a cross-sectional view showing an alternate assembly coupling the rod and the elongated member.

FIG. 9 is a cross-sectional view taken generally along line 9—9 of FIG. 8.

FIG. 10 is a cross-sectional view showing another assembly coupling the rod to the elongated member.

FIG. 11 is a side elevation view, partly in cross-section, of the insertion apparatus shown in FIG. 1 with the tip introduced into a fold of the IOL to be inserted into an eye.

FIG. 12 is a perspective view of a folding device shown in the open position.

FIG. 13 is a schematic perspective view showing the placement of the distal portion of the insertion tube in an eye.

FIG. 14 is a perspective view of an alternate folding device shown in the open position.

FIG. 15 is a side view, partly in cross-section, of an alternate tip.

DETAILED DESCRIPTION OF THE PREFERRED EMBODIMENTS

Figure 16:
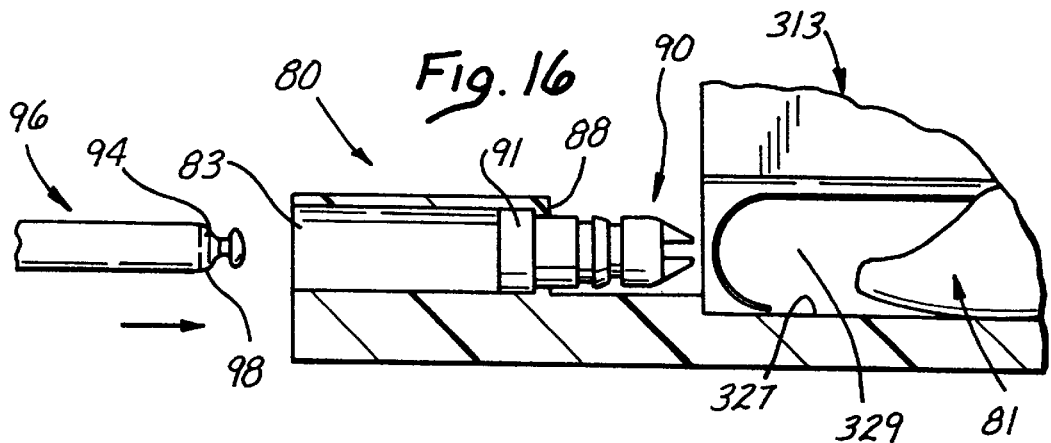
FIGS. 16 to 19 are a series of views, partly in cross-section, of the proximal portion of the alternate folding device shown in FIG. 14, in the closed position. Each of these Figs. show the rod and/or alternate tip at different locations in the process of using the alternate folding device to insert an IOL into an eye.
Figure 17:
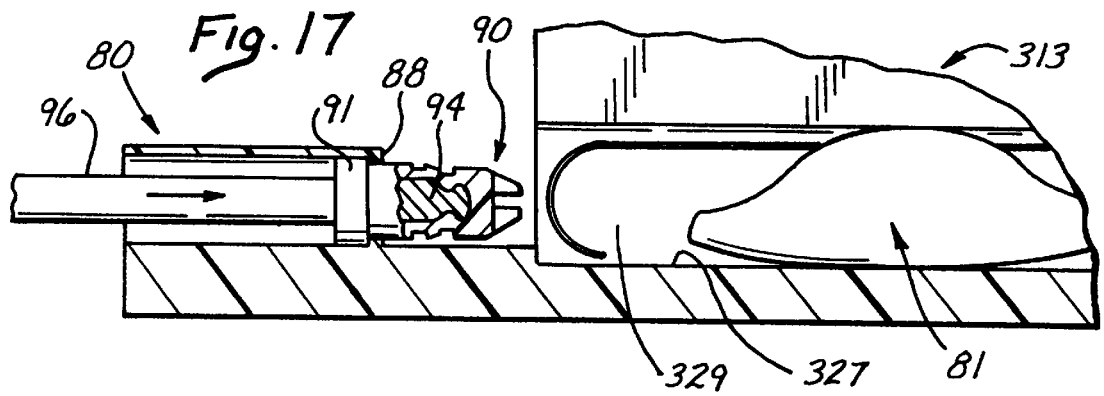

FIG. 1 illustrates an IOL insertion apparatus, shown generally as 10. The apparatus 10 comprises body 21, and a loading cartridge 13 including a forward tube 11 having an open port 12 at its distal end. The body 21 of injection apparatus 10 is an integrally formed unit. Loading cartridge 13 has folding leaves 14 and 15 which extend through opening 17 in the outer wall of the body 21. Proximal end portion 18 can be sized to completely and closely encompass plunger 19 of rod-plunger assembly 30, which has a plunger cap 20 affixed to its proximal end.

Proximal end portion 18 is hollow and includes a threaded surface 22, the threads of which matingly engage the threads 24 on the outer surface of plunger 19.

Insertion apparatus 10 includes a slot 23 which extends from the proximal portion of opening 17 and connects therewith. Slot 23 is elongated in a direction parallel to the longitudinal axis of insertion apparatus 10. Slot 23 is sufficiently wide to permit the closed folding members 51 and 52, shown in FIG. 12, to fit therethrough, and sufficiently long to permit loading cartridge 13 to be inserted therein, so that the loading cartridge can be subsequently moved into connecting opening 17, which is sufficiently narrow to hold the folding cartridge in a fully closed position.

As shown in FIG. 11, the distal end portion 25 of body 21 is hollow. When loading cartridge 13 is inserted into body 21, as shown in FIG. 11, the hollow space defined by the inner wall 27 of the body 21 is aligned with the hollow space 29 defined by the inner wall 31 of the loading cartridge 13. The combination of the joined body 21 and cartridge 13 can be considered a hollow tubular member defining a hollow space through which the elongated member can pass longitudinally.

FIG. 2 shows injector rod-plunger assembly 30 with locking enclosure 32a holding injector rod cap 32. Tip 34 is disposed on the distal end region 37 (FIG. 3) of the elongated member 35. Tip 34 is made of an elastomeric silicone polymer composition which is softer and more elastic than rod 33, which is made of titanium, and elongated member 35, which is made of a relatively polymeric material, such as reinforced polyamide, liquid crystal polymer and the like. For example, tip 34 is made of a material having a Shore A Hardness value in the range of about 40 to about 80 or about 90 or higher, more specifically about 70 to about 75. Viewed from a different perspective, the tip 34 preferably has a Shore A Hardness value within about 30 of the Shore A Hardness value of the material for which the optic of the IOL to be inserted is made.

With reference to FIG. 3, tip 34 has a length in the range of about 2 mm or about 5 mm to about 25 mm or about 50 mm, for example, about 10 mm. The length of tip 34 beyond the distal end 36 of elongated member 35 is in the range of about 0.25 mm to about 1.0 mm, for example, about 0.75 mm. Tip 34 is generally tapered in the distal direction, with the proximal end region 42 having an outer surface 44 which defines a larger cross-sectional area (transverse to longitudinal axis 46) than any other region of the tip. In addition, the distal end region 48 has an outer surface 50 (which extends to the distal end 52 of tip 34) which defines a smaller cross-sectional area than that defined by the outer surface 44 of the proximal end region 42. The outer surface of the tip 34 preferably is configured to facilitate holding or trapping of at least a portion of the tip in the IOL.

Elongated member 35 is sized and adapted to facilitate applying, for example, manually applying, the tip 34 to the plunger/rod assembly 30. The elongated member 35 preferably has sufficient length so as to be conveniently held in the hand of a human as the elongated member is being coupled to the rod 33. Particularly useful are elongated members having lengths in the range of about 0.5 cm or about 1 cm to about 5 cm or about 10 cm or longer.

The combination of tip 34 and elongated member 35 is preferably disposable after a single use, that is after being used to insert a single IOL into an eye. The other components of the IOL insertion apparatus 10, except for loading cartridge 13, are constructed, for example, of metal, so as to be reusable after sterilization.

The tip/elongated member combination can be made in any suitable manner, provided that the tip 34 is secured to the elongated member 35 and that both components and the combination function as described herein. In one particularly useful embodiment, the elongated member 35 is molded, for example, using conventional techniques, into the desired form and size. Preferably, the elongated member 35 includes a through hole 39 located in the distal end region 37. Once the elongated member 35 is formed, the tip 34 is secured to the distal end region 37, for example, using conventional insert molding techniques. The precursor material for the tip 34 is sufficiently flowable to fill the through hole 39. When this precursor material is cured, for example, using conventional techniques, the tip 34 is secured to the distal end region 34 of elongated member 35. The cured material in through hole 39 is part of tip 34 and facilitates the securing of the tip to the elongated member 35.

The distal end region 48 of tip 34 includes a slotted truncated cone structure 70. A cross slot 72 (FIG. 5) is placed in the truncated cone structure 70. This feature facilitates introducing the tip 34 into a fold of an IOL as the elongated member and tip combination is moved distally in the hollow space of a tube, as is described hereinafter. However, it should be noted that this slot structure 72 and the truncated cone structure 70 are not necessary in order to achieve substantial benefits in accordance with the present invention.

Elongated member 35 may be coupled to rod 33 in any suitable manner. The coupling between the elongated member 35 and the rod 33 should be sufficiently strong or secure so that these two components remain joined as the IOL insertion apparatus 10 is used to insert an IOL into an eye. For example, with reference to FIGS. 6 and 7 the proximal end region 41 of the elongated member 35 defines a hollow chamber 43 which terminates at end wall 45. Two spaced apart elements 47 and 49 are located near the distal end of the proximal end region 41. Elements 47 and 49 each include an inwardly extending segment 47a and 49a, respectively, which narrow the diameter of hollow chamber 43. Indents 47b and 49b are provided in elongated member 35 to facilitate a limited degree of flexing of elements 47 and 49, respectively. The distal end portion 36 of rod 33 includes a narrowed region 36a, an outwardly extending annular projection 36b and an intermediate diameter end region 36c.

The rod 33 and elongated member 35 are coupled or joined by passing the distal end portion 36 into the chamber 43. As the annular projection 36b comes into contact with segments 47a and 49a, elements 47 and 49 flex outwardly to allow the projection to pass distally. Once projection 36b is distal of segments 47a and 49a, elements 47 and 49 return to their normal positions. In so doing, projection 36b and end region 36c are held or trapped in the distal end region of the hollow chamber 43. Rod 33 is thus coupled or joined to elongated member 35 and is ready for use. The elements 47 and 49 are configured so that when desired, for example, after use, the rod 33 and elongated member 35 can be decoupled simply by pulling, in particular manually pulling, these two components apart.

The embodiment illustrated in FIGS. 8 and 9 utilize an interference or friction fit to couple or join the rod and the elongated member. Except as expressly described herein, this embodiment is substantially similar to that illustrated in FIGS. 6 and 7. Corresponding components are indicated by corresponding reference numerals increased by 100.

With reference to FIGS. 8 and 9, spaced apart elements 147 and 149 are positioned a substantially uniform distance apart along their lengths terminating at distal end wall 145. This substantially uniform distance is less than the diameter of the hollow chamber 143 distally of elements 147 and 149. The distal most segment 46 of distal end portion 136 of rod 133 has a substantially uniform diameter which substantially corresponds in size to the distance between elements 147 and 149. Thus, rod 133 is coupled or joined to elongated member 135 by passing the rod into chamber 143. As the distal most region 46 passes between elements 147 and 149, the distal end portion 136 becomes entrapped. The elements 147 and 149 are configured so that when desired the elements can be flexed apart and the rod 133 can be pulled out of chamber 143 to decouple the rod and elongated member 135.

The embodiment illustrated in FIG. 10 utilizes a threaded engagement to couple or join the rod and the elongated member. Except as expressly described herein, this embodiment is substantially similar to that illustrated in FIGS. 6 and 7. Corresponding components are indicated by corresponding reference numerals increased by 200.

With reference to FIG. 10, a distal region of the inner wall 48 defining hollow chamber 243 extends further inwardly than the remainder of the inner wall and is threaded. The distal end portion 236 is threaded so as to threadably engage the threads on inner wall 48. Thus, rod 233 is coupled or joined to elongated member 235 by passing the rod into chamber 243 and threading distal end portion 236 onto inner wall 48. When desired, the rod 233 can be decoupled from elongated member 235 simply by unthreading distal end portion 236 from inner wall 48.

FIG. 12 illustrates the manner in which loading cartridge 13 produces the desired result of folding IOL 57. Hinged folding leaves 14 and 15 are used to open and close folding members 51 and 52, respectively. IOL 57 (in an unfolded state) is placed on folding members 51 and 52, by forceps 59. The forceps 59 hold the IOL 57 in a specific and determinable planar orientation. Superior haptic 61 is placed forward of optic 63, while the other haptic 65 trails the optic, as shown in FIG. 12. Hinged folding leaves 14 and 15 are moved together, which folds the flexible or foldable optic 63 of IOL 57 in half. After IOL 57 is folded, the forceps 59 is removed.

The closed loading cartridge 13, containing the folded IOL 57, is then loaded into body 21 of insertion apparatus 10, as described above. An effective amount of a lubricant composition, such as a visco-elastic material, for example, a conventional sodium hyaluronate-containing aqueous material, preferably is included in the hollow space defined by the loading cartridge 13. This lubricant composition allows the folded IOL 57 to more easily pass through the hollow space defined by loading cartridge 13.

Insertion apparatus 10 is operated and functions as follows. When it is desired to insert IOL 57 into an eye, the apparatus 10 is placed in a configuration as shown in FIG. 1, with elongated member 35 (with tip 34) secured to rod 33, as shown in FIG. 2.

With the IOL 57 in its folded condition within apparatus 10, the operator (surgeon) advances plunger 19 distally by rotating cap 20. This action advances rod 33 and elongated member 35 distally. As rod 33 and elongated member 35 are moved distally, the tip 34 comes into contact with folded optic 63 and is introduced into the fold of the folded optic as shown in FIG. 11. Because of the relative softness and elasticity of tip 34, the distal movement of rod 33 and elongated member 35 causes the tip to become trapped in the fold of the folded optic 63. The folded optic 63 can be considered to be pulled or carried by the rod 33, elongated member 35 and tip 34 when the tip is trapped in the fold.

Referring now to FIG. 13, the IOL 57 is to be placed in eye 73 into an area formerly occupied by the natural lens of the eye. With the IOL 57 in its folded position within apparatus 10, and tip 34 trapped in the fold of the folded optic 63, forward tube 11 is ready for insertion through an incision in the sclera 75 of eye 73. Capsular bag 74 protects the posterior segment of the eye 73. With the forward tube 11 inserted within the eye 73 and the port 12 positioned so that the IOL 57 can unfold in the location within the eye 73 best suited for permanent implantation, the operator advances plunger 19 by rotating cap 20. This action advances rod 33, elongated member 35, tip 34 and IOL 57 distally into the forward tube 11.

As rod 33 advances farther distally, the IOL exits the port 12 in a controlled manner and is controllably released in a location as close as possible to the IOL's final implanted position.

FIG. 13 shows the sclera 75 having an incision through which the distal end portion of forward tube 11 is passed. Alternately, the incision can be made through the cornea or other portion of the eye. Forward tube 11 has a sufficiently small cross-section to pass into the eye 73 through a 3.0 mm incision in the sclera 102. Folding leaves 14 and 15, in contact with each other when lens loading cartridge 13 is in a closed position, can be grasped by an operator and used to guide and position insertion tube 11 in its desired position within the eye.

After IOL 57 has been inserted into eye 73, forward tube 11 is removed from the eye. The tip 34 can be used to position the IOL 57 in the eye. For example, the tip 34 can be retracted (after the optic is released) and then used to push the trailing haptic 65 out of the tube and position this haptic into the eye. If needed, IOL 57 can be repositioned in the eye by a small, bent needle or similar tool inserted into the same incision.

Once IOL 57 is properly positioned in eye 73 and apparatus 10 is withdrawn from the eye, the incision in the sclera may be closed, for example, using conventional techniques. After use, loading cartridge 13 and elongated member 35 (including tip 34) are preferably disposed of. Remaining portions of apparatus 10 can be reused after sterilization and disinfection.

FIGS. 14 and 16 to 19 show an alternate loading cartridge 313. Except as expressly described herein loading cartridge 313 is structured substantially similar to loading cartridge 13. Corresponding components are indicated by corresponding reference numerals increased by 300.

The primary difference between loading cartridge 313 and loading cartridge 13 is the presence of proximal member 80. Although proximal member 80 can be secured to the remainder of loading cartridge 313 in any suitable manner, it is preferred that this proximal member be integrally formed, for example, molded, with the remainder of the loading cartridge. Proximal member 80 includes a cylindrical component 82 which defines a hollow through compartment 83. As can be seen in FIGS. 16 to 19, hollow compartment 83 is aligned with the hollow space 329 defined by the inner wall 327 of loading cartridge 313. In particular, proximal member 80 is situated adjacent to folding member 352 so that when the loading cartridge 313 is placed in the closed position the hollow through compartment 83 is directly aligned with the hollow space 329 defined by the inner wall 327 of the closed loading cartridge 313.

Referring now to FIGS. 16 to 19, proximal member 80 includes a distal end opening 86 including an inwardly extending lip 88 which slightly reduces the size of the distal opening 86. Hollow through compartment 83 is sized and adapted to allow tip 90 to be passed distally through the hollow through compartment and to be situated as shown in FIG. 16. Alternately, the tip 90 can be located, for example, during storage, entirely within hollow through compartment 83. The proximal most portion 91 of tip 90 is held in hollow through compartment 83 because it has an increased diameter relative to the outside diameter of distal opening 86.

With reference to FIG. 15, tip 90 includes an irregularly shaped inner surface 92 which defines an irregularly shaped blind bore 93 which is compatible with the shape of the distal end portion 94 of rod 96 (FIGS. 16 to 19). The blind bore 93 is open at the proximal end 99 of tip 90. The inner surface 92 is configured to mate with the outer surface 98 of the distal end portion 94 of rod 96. Inner surface 92 includes a slightly enlarged flared region 100 which facilitates placing the distal end portion 94 of the rod 96 into the blind bore 93 defined by the inner surface 92. Tip 90 include distal annular indents 101 and 102 which are effective in facilitating introducing the tip into a fold of a folded IOL and in facilitating holding the tip in the fold of the IOL. With the outer surface 98 of the distal end portion 94 of rod 96 mated to the inner surface 92 defining the blind bore 93, tip 90 is secured to rod 96.

Tip 90 is configured substantially similar to tip 34, with the exception that the distal most portion 91 of tip 90 is substantially shorter than the distal most portion of tip 34.

The combination of loading cartridge 313 and tip 90 can be packaged as a unit. Thus, this combination can be manufactured, sterilized and packaged so as to be ready for use in a single IOL insertion procedure.

The combination of loading cartridge 313 and tip 90 is used as follows. For the purposes of this discussion, rod 96 is secured directly to plunger 19 in a manner similar to the securement between plunger 19 and rod 33. In addition, IOL 81 is loaded into loading cartridge 313 in a manner similar to that in which IOL 57 is loaded into loading cartridge 13. Once the loading cartridge 313 has been loaded with IOL 81, it is placed in the body 21 of IOL insertion apparatus 10. An effective amount of a lubricant composition is included in the loading cartridge 313, as described previously. For the sake of clarity, FIGS. 16 to 19 do not show the body 21.

Referring now to FIGS. 16 to 19 with regard to the operation of loading cartridge 313, FIG. 16 shows the rod 96 proximally of the loading cartridge 313 which includes the folded IOL 81. As rod 96 is moved distally through the hollow through compartment 83 it comes in contact with tip 90. Because of the mating configurations noted above, the distal end portion 94 of rod 96 completely fills the blind bore 93 defined by inner wall 92. As the rod 96 continues to be moved distally, this movement overcomes the resistance caused by lip 88. Since tip 90 is made of a elastomeric silicone polymeric material, it is somewhat compliant so that the distal most portion 91 of tip 90 passes out of hollow through compartment 83.

Figure 18:
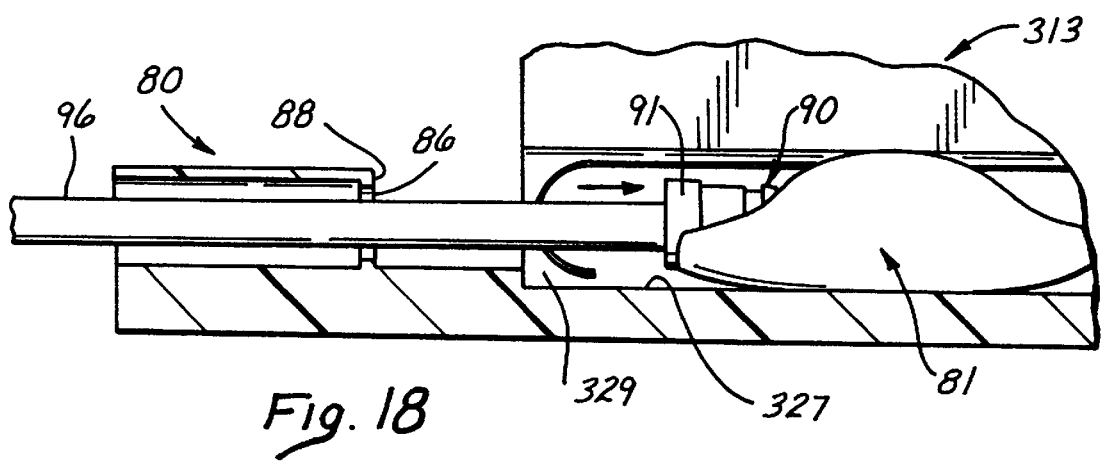
Figure 19:
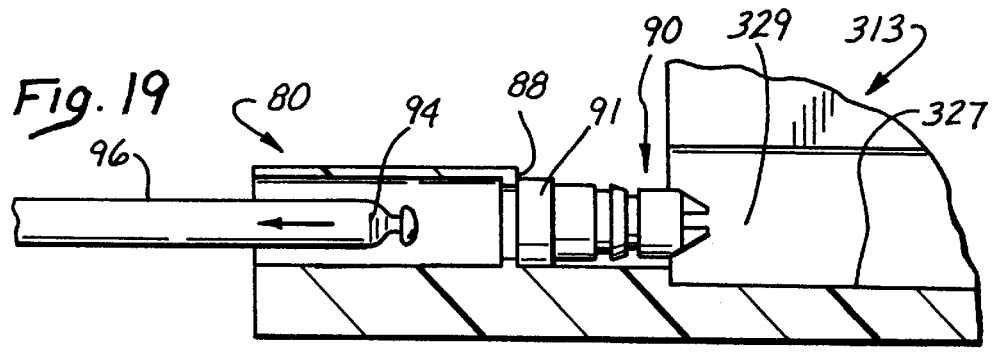

With reference to FIG. 18, as rod 96 continues to be moved distally, tip 90 is introduced into the fold of folded IOL 81. Rod 96 is moved still further distally to cause the IOL to be passed through the hollow space 329 defined by the inner wall 327 of loading cartridge 313 and into the eye. Once the folded IOL 81 has been inserted into the eye, rod 96 is moved proximally through the hollow space 329 defined by the inner wall 327 of loading cartridge 3132 and into and through the hollow through compartment 83 of proximal member 80. As shown in FIG. 19, as the distal end portion 94 of rod 96 passes into the hollow through compartment 82, the proximal most portion 91 of tip 90 contacts lip 88. This causes the tip 90 to become separated from rod 96. At this point, since the IOL 81 has been inserted, the loading cartridge 313 and tip 90 can be removed from the body 21 of apparatus 10 and disposed of, while the remainder of the components of apparatus 10 can be sterilized and/or otherwise prepared for reuse.

While this invention has been described with respect to various specific examples and embodiments, it is to be understood that the invention is not limited thereto and that it can be variously practiced within the scope of the following claims.

What is claimed is:

1. An apparatus for inserting a folded intraocular lens into an eye comprising:

a tube defining a hollow passage and having a port through which the intraocular lens is passed from said hollow passage into an eye;

an elongated member longitudinally movable within said hollow passage, having a distal end portion and a proximal end portion and being adapted to be disposed of after a single use;

a rod which is longitudinally movable relative to said tube and is adapted to be repeatedly reused and has a distal end region non-destructively and removably coupled to said elongated member at said proximal end portion; and a tip secured to said elongated member and extending distally from said distal end portion, said tip being softer than said distal end portion and being sized and configured so that said tip comes in contact with the folded intraocular lens as said elongated member is moved distally in said hollow passage, said tie including a proximal end segment having a first outer surface defining a first cross-sectional area and a distal end segment having a second outer surface defining a second cross-sectional area smaller than said first cross-sectional area.

2. The apparatus of claim 1 wherein said tip is more elastic than said distal end portion and is permanently secured to said elongated member.

3. The apparatus of claim 1 wherein said tip is sized and configured so that at least a portion of said tip is introduced into a fold of the folded intraocular lens as said elongated member is moved distally in said hollow passage.

4. The apparatus of claim 1 wherein said tip is sized and configured so that at least a portion of said tip is held in a fold of the folded intraocular lens as said elongated member is moved distally in said hollow passage.

5. The apparatus of claim 4 wherein said proximal end segment is longer than all the other segments of said tip combined.

6. The apparatus of claim 1 wherein said elongated member includes a through hole and a portion of said tip is located in said through hole, thereby facilitating a permanent securement of said tip to said elongated member.

7. The apparatus of claim 1 wherein said elongated member includes a plurality of spaced apart elements defining a cavity in which said distal end region of said rod is maintained.

8. The apparatus of claim 7 wherein said plurality of spaced apart elements and said distal end region are configured to facilitate said distal end region passing into said cavity as said rod is moved longitudinally toward said elongated member and to resist said distal end region passing out of said cavity as said rod is moved longitudinally away from said elongated member.

9. The apparatus of claim 7 wherein said plurality of spaced apart elements are adapted to flex as said distal end region is passed distally into said cavity.

10. The apparatus of claim 7 wherein said distal end region of said rod is interference fitted into said cavity.

11. The apparatus of claim 1 wherein said distal end region of said rod is interference fitted to said elongated member.

12. The apparatus of claim 1 wherein said distal end region of said rod is threaded and said elongated member includes threads which matingly engage said distal end region.

13. The apparatus of claim 1 wherein said rod is made of metal.

* * * * *

UNITED STATES PATENT AND TRADEMARK OFFICE
CERTIFICATE OF CORRECTION

PATENT NO. : 6,056,758
DATED : May 2, 2000
INVENTOR(S) : Vidal et al.

It is certified that error appears in the above-identified patent and that said Letters Patent is hereby corrected as shown below:

<u>Column 12,</u>
Line 14, delete "tie" and insert -- tip --.

Signed and Sealed this

Twelfth Day of August, 2003

JAMES E. ROGAN
*Director of the United States Patent and Trademark Office*